United States Patent [19]
Koeda et al.

[11] Patent Number: 5,735,794
[45] Date of Patent: Apr. 7, 1998

[54] ENDOSCOPE HAVING EXTERNAL BATTERY CONNECTED TO BATTERY CASING

[75] Inventors: Takashi Koeda; Hiroshi Sano; Hirohisa Ueda; Kunitoshi Ikeda; Kunikiyo Kaneko; Rensuke Adachi, all of Tokyo, Japan

[73] Assignee: Asahi Kogaku Kogyo Kabushiki Kaisha, Tokyo, Japan

[21] Appl. No.: 629,777

[22] Filed: Apr. 9, 1996

[30] Foreign Application Priority Data

Apr. 19, 1995 [JP] Japan .................. 7-092913

[51] Int. Cl.⁶ .................................. A61B 1/06
[52] U.S. Cl. .................................. 600/178; 600/132
[58] Field of Search .................. 600/131–132, 600/160, 178–180, 199, 249; 607/90, 151

[56] References Cited

U.S. PATENT DOCUMENTS

| | | | |
|---|---|---|---|
| 1,625,356 | 4/1927 | Geulen | 600/249 |
| 2,102,274 | 12/1937 | Larimore | 600/179 X |
| 2,235,979 | 3/1941 | Brown | 600/178 |
| 2,236,842 | 4/1941 | Allyn | 600/178 |
| 2,507,935 | 5/1950 | Richmond | 600/178 X |
| 3,005,452 | 10/1961 | Pitman | 600/179 |
| 3,021,835 | 2/1962 | Rose | 600/178 |
| 4,580,198 | 4/1986 | Zinnanti, Jr. | 362/203 |
| 5,115,261 | 5/1992 | Noda et al. | |
| 5,159,380 | 10/1992 | Furuya et al. | |
| 5,170,775 | 12/1992 | Tagami | 600/178 |
| 5,184,159 | 2/1993 | Furuya et al. | |
| 5,184,170 | 2/1993 | Takahashi et al. | |
| 5,191,369 | 3/1993 | Furuya et al. | |
| 5,220,912 | 6/1993 | Nakasima et al. | |
| 5,272,497 | 12/1993 | Furuya et al. | |
| 5,394,865 | 3/1995 | Salerno | 600/199 |
| 5,542,904 | 8/1996 | Heine et al. | 600/199 X |

Primary Examiner—Richard J. Apley
Assistant Examiner—John P. Leubecker
Attorney, Agent, or Firm—Greenblum & Bernstein

[57] ABSTRACT

A portable endoscope system has an illuminating light guide for transmitting light for illuminating an object. A light source lamp contained in an illuminating light supply unit supplies light to the illuminating light guide. The entrance end portion of the illuminating light guide is disposed in an endoscope control part. The illuminating light supply unit is detachably attached to the control part. The portable endoscope system includes a connecting cable which connects the light source lamp with an external battery to supply electricity to the light source lamp from outside the endoscope system.

9 Claims, 5 Drawing Sheets

ENDOSCOPE HAVING EXTERNAL BATTERY CONNECTED TO BATTERY CASING

BACKGROUND OF THE INVENTION

The present disclosure relates to subject matter contained in Japanese Patent Application No. 7-92913 (filed on Apr. 19, 1995), which is expressly incorporated herein by reference in its entirety.

1. Field of the Invention

The present invention relates to a portable endoscope system in which a unit for supplying illuminating light to a light guide is attached to an endoscope control part.

2. Description of the Related Art

A conventional portable endoscope system has a light-emitting device for illumination which is provided in an endoscope control part. In such a portable endoscope system, an illuminating light supply unit, which contains a miniature bulb and a dry battery as a power supply for the bulb, is attached to the control part. This enables an endoscopic inspection (endoscopy) to be conducted even in a place where no commercial AC power supply is available.

However, such an illuminating light supply unit can only hold a small battery. Therefore, the battery may run down in a short time of use; and hence the illumination becomes dark in the middle of an endoscopy, making it impossible to continue.

In such a case, it is extremely troublesome for the doctor to replace the battery during the endoscopy, and it is considerably painful to the patient to be kept waiting during that time. If there is no spare battery, the endoscopy must be stopped. Thus, the prior art presents a serious problem.

SUMMARY OF THE INVENTION

An object of the present invention is to provide a portable endoscope system which enables an endoscopy to be conducted even in a place where no commercial AC power supply is available without the need for battery replacement for a long period of time, and which has no likelihood that an endoscopy will be interrupted by battery replacement as in the case of the prior art.

Other objects and advantages of the present invention will become apparent from the following detailed description of an illustrated embodiment of the invention.

According to the present invention, there is provided a portable endoscope system having an illuminating light guide for transmitting light for illuminating an object. A light source lamp contained in an illuminating light supply unit supplies illuminating light to the illuminating light guide. The entrance end portion of the illuminating light guide is disposed in an endoscope control part. The illuminating light supply unit is detachably attached to the control part. The portable endoscope system includes a connecting cable for connecting the light source lamp with an external battery for supplying electrical energy to the light source lamp from outside the portable endoscope system.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

An embodiment of the present invention will be described below with reference to the accompanying drawings.

Figure 1:
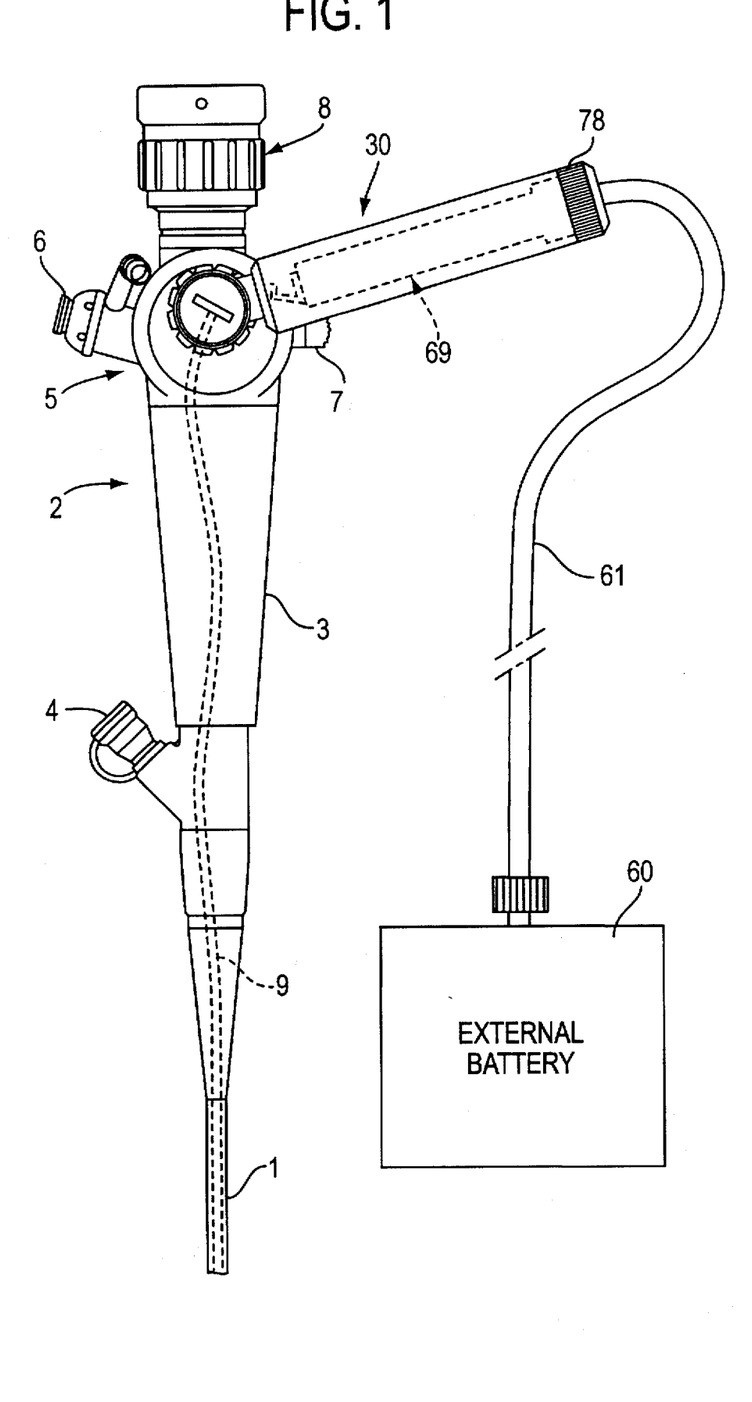
FIG. 1 is a side view showing an embodiment of the portable endoscope system according to the present invention with an illuminating light supply unit attached to an endoscope control part.

Referring to FIG. 1, a portable endoscope system according to an embodiment of the present invention has an insert part 1 which is covered with a flexible tube, and a control part 2 which is connected to the proximal end of the insert part 1. About three fourths of the way from the bottom of the control part 2 is a grip portion 3. A forceps inlet 4 is provided between the grip portion 3 and the insert part 1 so as to project obliquely forward.

The control part 2 has a control mechanism portion 5 above the grip portion 3. The control mechanism portion 5 has a suction control valve 6 which is disposed on the front side thereof to carry out a suction operation through a forceps channel (not shown) inserted in the insert part 1. The control mechanism portion 5 further has a bending control lever 7 which is disposed on the rear side thereof to control a remote-controlled bendable portion (not shown) which is formed at the distal end of the insert part 1. In addition, an eyepiece 8 is provided on the top of the control mechanism portion 5.

A light guide fiber bundle 9 for transmitting light for illuminating an object has an entrance end portion thereof disposed in the control mechanism portion 5, and extends through the insert part 1 and the grip portion 3 of the control part 2. The exit end portion of the light guide fiber bundle 9 is disposed in the distal end of the insert part 1.

An illuminating light supply unit 30 for supplying illuminating light to the light guide fiber bundle 9 is detachably attached to a side of the control mechanism portion 5.

The illuminating light supply unit 30 contains a light source lamp that emits illuminating light supplied to the light guide fiber bundle 9, and a battery serving as a power supply for lighting the light source lamp. In the present invention, however, the built-in battery is removed from the illuminating light supply unit 30, and a connecting cable 61 connects an external battery 60 to the illuminating light supply unit 30.

Figure 2:
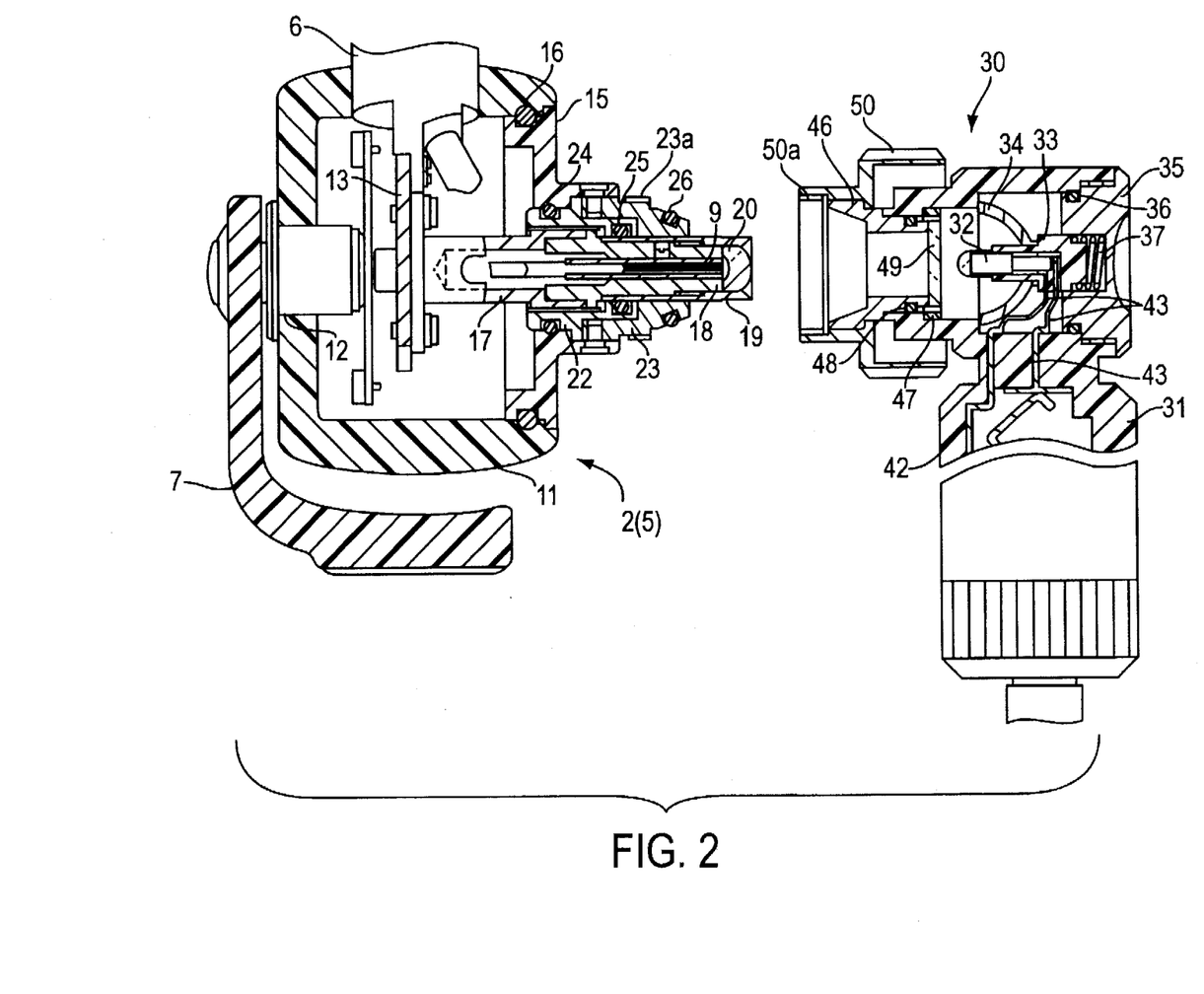
FIG. 2 is an enlarged sectional plan view showing the embodiment of the present invention with the illuminating light supply unit detached from the endoscope control part.

FIG. 2 is an enlarged sectional view showing the portable endoscope system in a state where the illuminating light supply unit 30 is detached from the control part 2.

The control mechanism portion 5 of the control part 2 is covered with a casing 11 made of a plastic material. A lever bearing cylinder 12 that supports the bending control lever 7 is fitted in a through-hole provided in the casing 11, and sealed in a watertight manner. Similarly, the suction control valve 6 is fitted in a through-hole provided in the casing 11, and sealed in a watertight manner. The respective proximal end portions of the lever bearing cylinder 12 and the suction control valve 6 are secured to a frame 13 in the control part 2.

A cover 15 is fitted in a relatively large opening provided in a side of the casing 11, and a sealing O-ring 16 is attached to the fitting surface of the cover 15 to prevent water from entering the inside of the control part 2 through the gap between the cover 15 and the peripheral wall of the opening. It should be noted that, although the O-ring 16 is compressed when held between the cover 15 and the casing 11, the cross-sectional configuration of the O-ring 16 shown in the figures is in a natural state before it is compressed (the same shall apply hereinafter).

A support cylinder 17 is disposed on the central axis of a bore formed in the center of the cover 15. The proximal end portion of the support cylinder 17 is secured to the frame 13 in the control part 2. A light guide mounting cylinder 18 is screwed to the support cylinder 17. The distal end portion of the light guide mounting cylinder 18 projects outwardly from the support cylinder 17. The entrance end portion of the light guide fiber bundle 9 is secured with a screw at the central axis position in the light guide mounting cylinder 18.

A lens mounting cylinder 19 is fitted on the projecting end portion of the light guide mounting cylinder 18 in a cap-like fashion, and firmly thread-engaged with it. The lens mounting cylinder 19 has a convex meniscus lens 20 which is bonded to the distal end portion thereof in a watertight manner. Thus, the convex meniscus lens 20 is set at a position close to the entrance end surface of the light guide fiber bundle 9 so as to face it.

An O-ring retaining frame 22 is disposed to surround the joint between the support cylinder 17 and the light guide mounting cylinder 18. The O-ring retaining frame 22 is fitted at the outer surface thereof to the wall of the bore provided in the center of the cover 15, and fitted at the inner surface thereof to the outer surface of the lens mounting cylinder 19. O-rings 24 and 25 are attached to the outer and inner surfaces, respectively, of the O-ring retaining frame 22 to prevent water from entering the inside of the control part 2 through the gap between the O-ring retaining frame 22 and the cover 15 or through the gap between the O-ring retaining frame 22 and the lens mounting cylinder 19.

A connecting cylinder 23 is disposed to surround an area which extends from the lens mounting cylinder 19 to the O-ring retaining frame 22. The proximal end portion of the connecting cylinder 23 is screwed to the inner surface of the bore in the cover 15. The outer peripheral surface of an intermediate portion of the connecting cylinder 23 is provided with an external thread 23a. The outer peripheral surface of the distal end portion of the connecting cylinder 23, which lies forward of the external thread 23a, is a tapered surface which becomes gradually smaller in diameter toward the distal end. A sealing O-ring 26 is attached to the tapered surface at an intermediate position between the external thread 23a and the distal end.

The illuminating light supply unit 30 has an L-shaped cylindrical configuration. The illuminating light supply unit 30 has a plastic casing 31. A light source lamp 32 is disposed in the bend of the L-shaped casing 31, and is attached to a lamp socket 33.

The light source lamp 32 is disposed on the axis of the short cylindrical portion of the L-shaped casing 31. A reflecting mirror 34 is attached to the lamp socket 33 so as to surround the light source lamp 32 to converge illuminating light from the light source lamp 32 on the axis of the short cylindrical portion of the L-shaped casing 31.

The casing 31 is formed with an opening behind the lamp socket 33. A bottom cover 35 is detachably thread-engaged with the mouth of the opening. A sealing O-ring 36 is disposed between the fitting surfaces of the bottom cover 35 and the casing 31 to prevent water from entering the inside of the illuminating light supply unit 30 through the gap between the bottom cover 35 and the casing 31. In addition, a compression coil spring 37 is interposed between the bottom cover 35 and the lamp socket 33 to secure the lamp socket 33 and the reflecting mirror 34 by resilient force from the spring 37.

A receiving cylinder 46 is secured in an opening provided at the end of the short cylindrical portion of the L-shaped casing 31 by fastening a nut 47 from the inner side of the casing 31. The receiving cylinder 46 has a tapered opening which engages the tapered surface of the connecting cylinder 23, which is provided on the control part 2.

A sealing O-ring 48 is disposed between the fitting surfaces of the receiving cylinder 46 and the casing 31 to prevent water from entering the inside of the illuminating light supply unit 30 through the gap therebetween. A plane-parallel transparent plate 49 is bonded to the inner end portion of the receiving cylinder 46 in a watertight manner. Thus, the illuminating light supply unit 30 is formed into a watertight structure which prevents water from entering the illuminating light supply unit 30 through any portion thereof.

Further, a fastening ring 50 is attached to the outer peripheral portion of the receiving cylinder 46 to prevent it from dislodging axially. The fastening ring 50 has an internal thread 50a for engagement with the external thread 23a of the connecting cylinder 23.

Accordingly, to connect the illuminating light supply unit 30 to the control part 2, the tapered surfaces of the connecting cylinder 23 and the connecting cylinder receiving cylinder 46 are brought into close contact with each other. Then, the internal thread 50a of the fastening ring 50 is engaged with the external thread 23a of the connecting cylinder 23. Thus, the illuminating light supply unit 30 is connected to the control part 2, as shown in FIG. 3.

In the portable endoscope system having the illuminating light supply unit 30 attached to the control part 2 as described above, illuminating light that is emitted from the light source lamp 32 is reflected by the reflecting mirror 34, and then passes through the transparent plate 49 and the convex meniscus lens 20. Thus, the illuminating light converges on the entrance end surface of the light guide fiber bundle 9, and enters the light guide fiber bundle 9.

Since the cylinder 23 and the connecting receiving cylinder 46 are brought in close contact with each other at the respective tapered surfaces, the illuminating light supply unit 30 can be secured fixedly to the control part 2 by tightly fastening the fastening ring 50 to the connecting cylinder 23.

Figure 3:
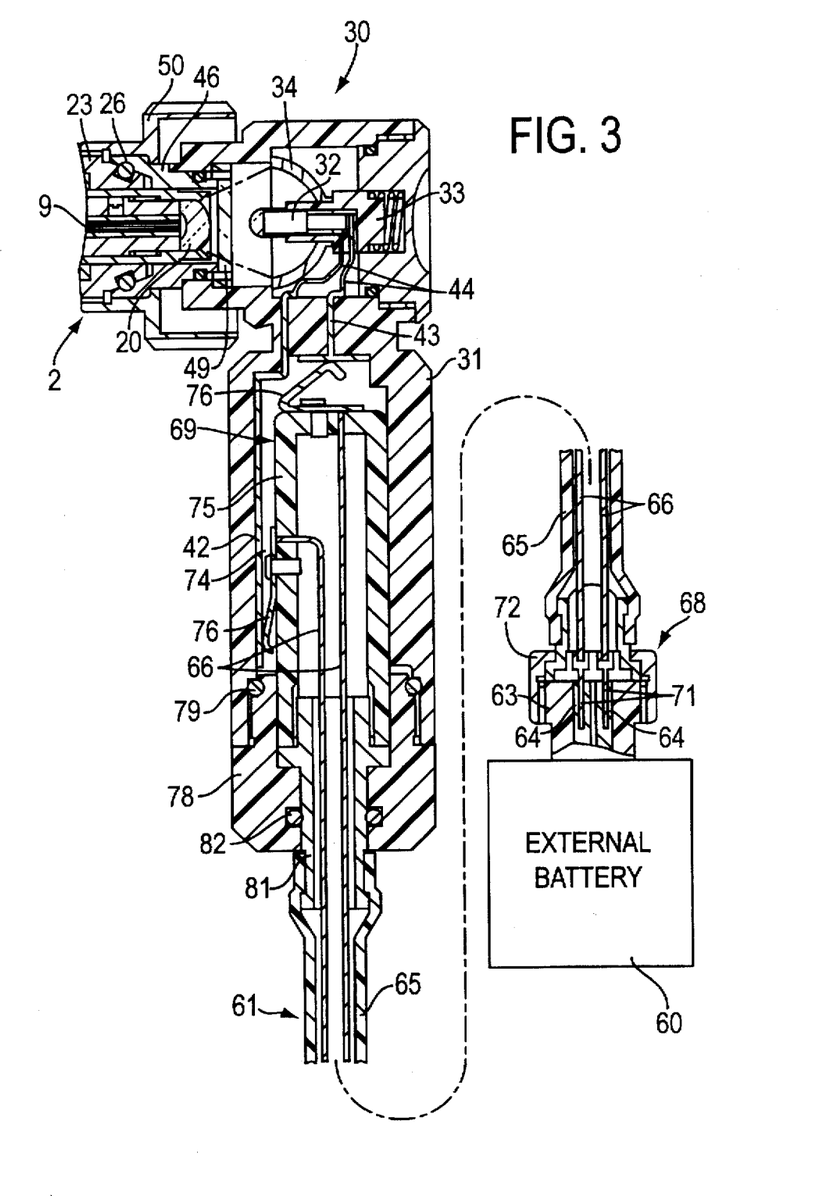
FIG. 3 is an enlarged sectional plan view showing the embodiment of the present invention with the illuminating light supply unit attached to the endoscope control part.
Figure 4:
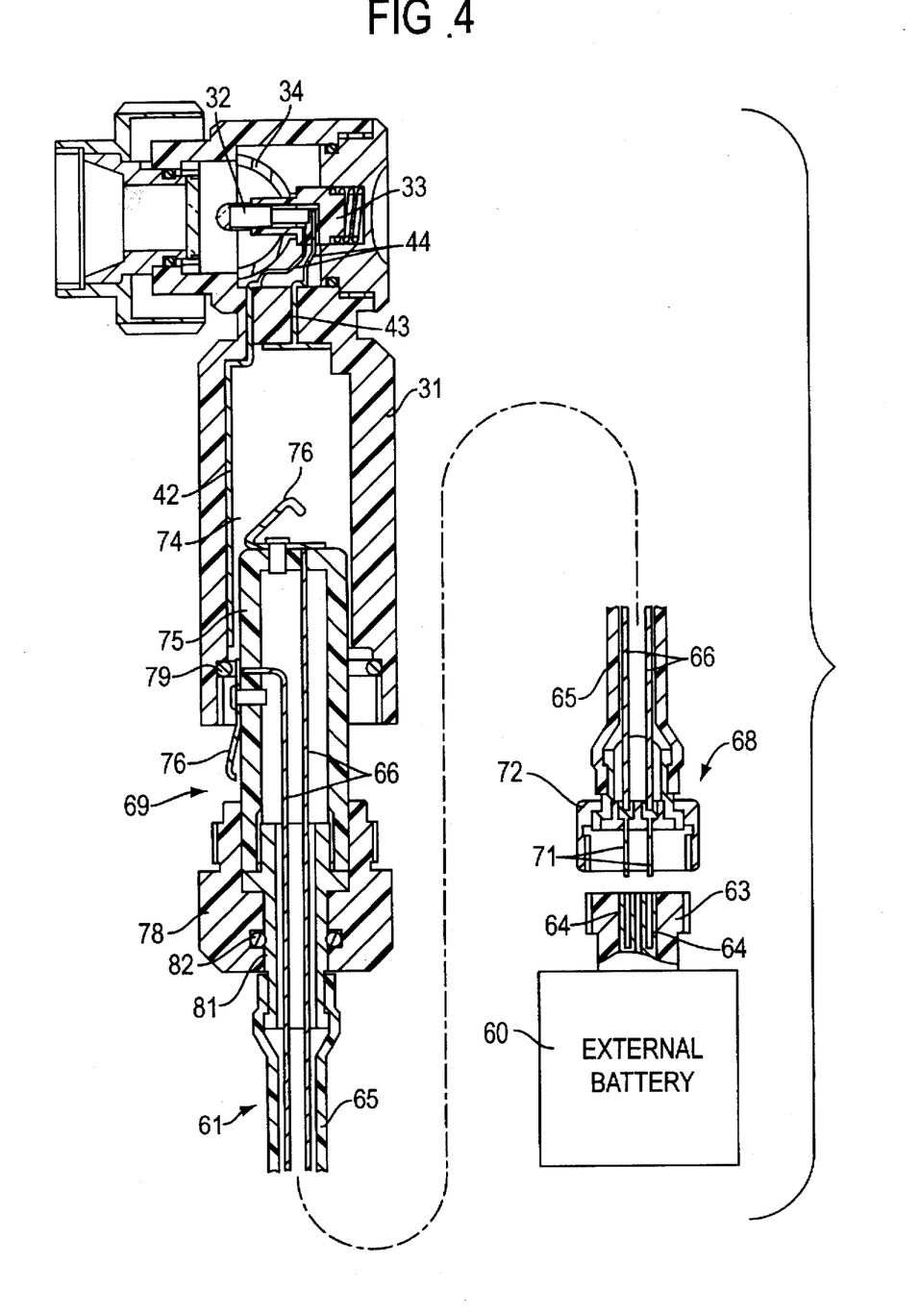
FIG. 4 is an enlarged sectional plan view showing the embodiment of the present invention in a state where the illuminating light supply unit is disconnected from an external battery.

FIG. 3 shows the attached arrangement of the illuminating light supply unit 30. FIG. 4 shows the illuminating light supply unit 30 where connecting portions at both ends of the connecting cable 61 are disconnected from the illuminating light supply unit 30 and the external battery 60.

The external battery 60 is a battery provided outside the endoscope system. It is possible to use a battery of large capacity, a group of batteries of small capacity, an automotive battery, etc.

The connecting cable 61 is formed from two electric wires 66 which are inserted in a flexible tube 65. The connecting cable 61 has connectors 68 and 69 which are attached to both its ends, respectively.

The connector 68, which is connected to the external battery 60, is provided with two contact pins 71 for connecting the electric wires 66 to contacts 64. The connector 68 is connected to the external battery 60 by thread-engaging a fastening ring 72 with an output terminal portion 63, and disconnected therefrom by undoing the thread engagement.

The connector 69, which is connected to the illuminating light supply unit 30, has an electrically insulating plug body 75 which is removably inserted into a battery casing 74 formed in the long cylindrical portion of the L-shaped illuminating light supply unit 30. The plug body 75 has two contacts 76 which are connected to the electric wires 66, respectively. When the plug body 75 is inserted into the battery casing 74, the two contacts 76 contact with respective electrodes 42 and 43 provided in the casing 31. The electrodes 42 and 43 are connected to the light source lamp 32 through respective lead wires 44.

It should be noted that a switch (not shown) for controlling the light source lamp 32 is provided in an intermediate portion of the wiring for supplying electric power to the light source lamp 32. The switch is also sealed in a watertight manner so that no water can enter the inside of the illuminating light supply unit 30.

The plug body 75 has a cover 78 which is provided at the proximal end thereof. The cover 78 is thread-engaged with an opening provided at the distal end of the casing A sealing O-ring 79 is disposed in the boundary between the cover 78 and the casing 31. The plug body 75 is connected to the tube 65 of the connecting cable 61 by a connecting cylinder 81. A sealing O-ring 82 is disposed between the outer peripheral surface of the connecting cylinder 81 and the inner peripheral surface of the cover 78.

Thus, when the external battery 60 is connected to the illuminating light supply unit 30 by the connecting cable 61, the light source lamp 32 is lit by electrical energy supplied from the external battery 60, and light is supplied to the light guide fiber bundle 9.

Figure 5:
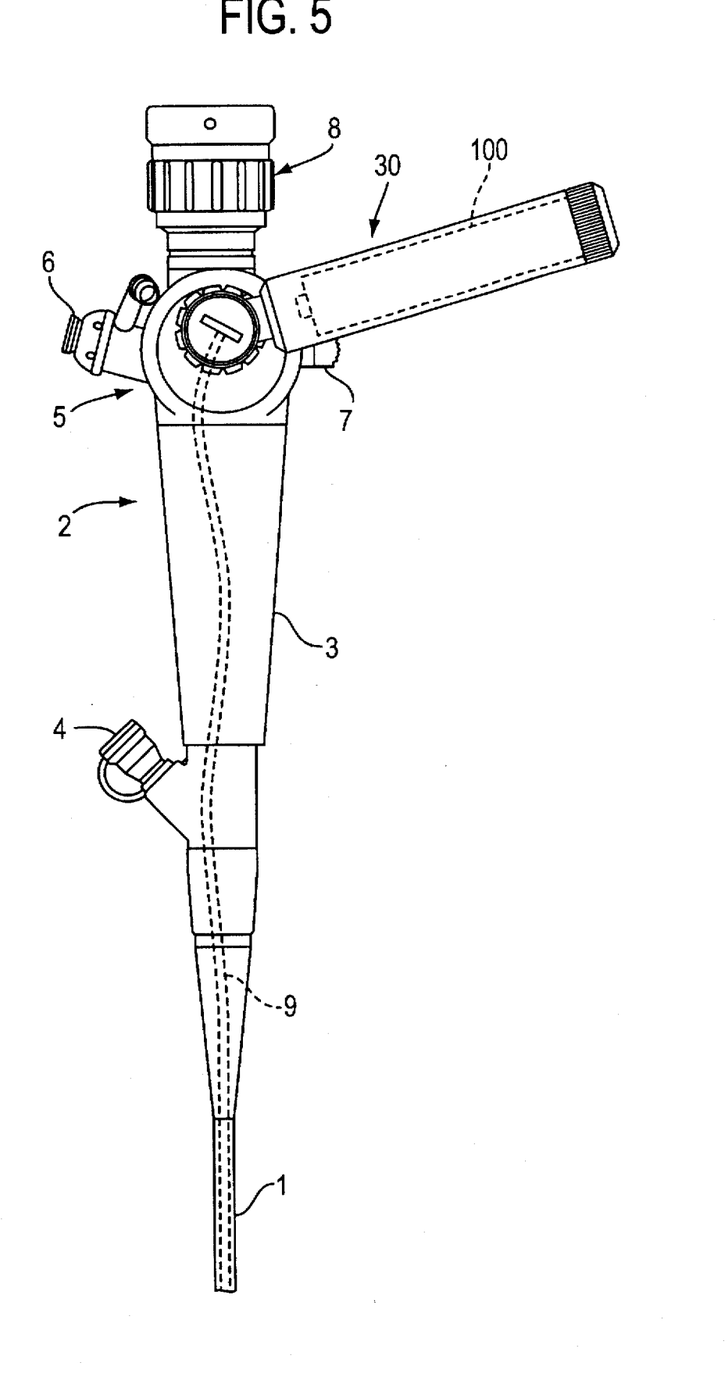
FIG. 5 is a side view showing the embodiment of the present invention in a state where a built-in battery is set in the illuminating light supply unit attached to the endoscope control part.

FIG. 5 shows the portable endoscope system where a battery 100 is set in the battery casing 74 of the illuminating light supply unit 30 in place of the connector 69. Thus, an appropriate power supply can be selectively used according to the circumstances.

According to the present invention, a connecting cable is provided to connect an external battery to the light source lamp of the portable endoscope system. Therefore, by using the external battery as a power supply for the light source lamp, an endoscopy can be conducted even in a place where no commercial AC power supply is available. Moreover, it is possible to use an external battery of large capacity if necessary. Therefore, an endoscopy can be smoothly conducted for a long period of time without a fear of interruption.

Further, if the system is arranged such that the connecting cable is detachable with respect to the illuminating light supply unit, it is possible to use another power supply, e.g. a built-in battery, as a power supply for the light source lamp according to the circumstances.

While the invention has been described by reference to a specific embodiment chosen for purposes of illustration, it should be apparent that numerous modifications could be made thereto by those skilled in the art without departing from the basic concept and scope of the invention.

We claim:

1. A portable endoscope system comprising:
   an illuminating light guide for transmitting light to illuminate an object, said illuminating light guide having an entrance end portion disposed in an endoscope control part;
   a light source lamp in an illuminating light supply unit for supplying illuminating light to said illuminating light guide, said illuminating light supply unit comprising a generally L-shaped cylindrical configuration having a first leg defined by a direction of light emission by said light source lamp and a second leg defined by a battery casing, and being detachably attachable to said endoscope control part;
   said battery casing having a first electrode at an end thereof and a second electrode at a side thereof; and
   a connecting cable for connecting said light source lamp with an external battery for supplying electricity to said light source lamp through said battery casing from outside said portable endoscope system, said cable having a first electrode at an end of said cable and a second electrode at a side of said cable to connect with said first and second electrodes of said battery casing, respectively, when said cable is connected to said battery casing.

2. A portable endoscope system according to claim 1, further comprising a connector for detachably connecting said connecting cable to said illuminating light supply unit.

3. A portable endoscope system according to claim 2, wherein said illuminating light supply unit includes a said battery casing accommodating a built-in battery, so that said light source lamp can be lit by electricity supplied from the built-in battery accommodated in said battery casing.

4. A portable endoscope system according to claim 3, wherein said connecting cable is connected to said illuminating light supply unit through a space defined in said battery casing when said built-in battery is not present.

5. A portable endoscope system according to claim 1, further comprising a connector for detachably connecting said connecting cable to said external battery.

6. A portable endoscope system comprising:
   an illuminating light guide for transmitting light to illuminate an object, said illuminating light guide having an entrance end portion disposed in an endoscope control part;
   a light source lamp in an illuminating light supply unit for supplying illuminating light to said illuminating light guide, said illuminating light supply unit being detachably attachable to said endoscope control part;
   said illuminating light supply having a battery casing, said battery casing having a first electrode at an end thereof and a second electrode at a side thereof and
   a connecting cable for connecting said light source lamp with an external battery for supplying electricity to said light source lamp from outside said portable endoscope system, said cable having a first electrode at an end of said cable and a second electrode at a side of said cable to connect with said first and second electrodes of said battery casing, respectively, when said cable is connected to said battery casing;
   a first connector which detachably connects said connecting cable to said illuminating light supply unit; and
   a second connector which detachably connects said connecting cable to said external battery.

7. The portable endoscope system according to claim 6, said illuminating light supply unit having a generally L-shaped cylindrical configuration with a first leg defined by a direction of light emitted by said light source lamp and a second light defined by said battery casing.

8. The portable endoscope system according to claim 6, said battery casing accommodating a built-in battery, so that said light source lamp can be lit by electrical energy supplied from the built in battery accommodated in said battery casing.

9. The portable endoscope system according to claim 8, said connecting cable being connected to said illuminating light supply unit through a space defined in said battery casing when said built in battery is not present within said battery casing.

* * * * *

UNITED STATES PATENT AND TRADEMARK OFFICE
CERTIFICATE OF CORRECTION

PATENT NO. : 5,735,794
DATED : April 7. 1998
INVENTOR(S) : T. KOEDA et al.

It is certified that error appears in the above-indentified patent and that said Letters Patent is hereby corrected as shown below:

At column 6, line 48 (claim 6, line 12), change "thereof" to ---thereof;---.

Signed and Sealed this

Twenty-first Day of July, 1998

Attest:

BRUCE LEHMAN

Attesting Officer

Commissioner of Patents and Trademarks